United States Patent
Propato et al.

(10) Patent No.: US 7,620,453 B1
(45) Date of Patent: Nov. 17, 2009

(54) IMPLANTABLE MEDICAL DEVICE WITH IMPROVED EMI FILTER

(75) Inventors: Claudio Propato, Saugus, CA (US); Gabriel A. Mouchawar, Valencia, CA (US); Chris Sorensen, Valencia, CA (US)

(73) Assignee: Pacesetter, Inc., Sylmar, CA (US)

(\*) Notice: Subject to any disclaimer, the term of this patent is extended or adjusted under 35 U.S.C. 154(b) by 400 days.

(21) Appl. No.: 11/551,664

(22) Filed: Oct. 20, 2006

(51) Int. Cl.
*A61N 1/16* (2006.01)
(52) U.S. Cl. .................. 607/37; 607/4; 607/5; 607/36; 128/901
(58) Field of Classification Search ................ 607/6, 607/116, 119, 1–2, 4–5, 8–9, 36–38, 63; 128/898, 899, 903; 318/400.24; 361/818; 720/650
See application file for complete search history.

(56) References Cited

U.S. PATENT DOCUMENTS 5,690,683 A * 11/1997 Haefner et al. ................. 607/4
5,817,130 A * 10/1998 Cox et al. ...................... 607/5
2005/0197677 A1 * 9/2005 Stevenson .................... 607/36

OTHER PUBLICATIONS

Dictionary.com. "attenuate" definition. Jul. 6, 2009 <http://dictionary.reference.com/browse/attenuate>.*

* cited by examiner

*Primary Examiner*—Carl H Layno
*Assistant Examiner*—Elizabeth K So

(57) ABSTRACT

An electromagnetic interference (EMI) filter is provided to attenuate potentially damaging high frequency electromagnetic interference from interfering with the operation of a hermetically sealed implantable medical device. In one embodiment, the EMI filter is joined to a bypass unit that is configured to provide an energy path for the delivery of an energy pulse. The bypass unit, in one embodiment, may include a non-linear device in parallel with an impedance component. The non-linear device can be a DIAC, a MOSFET, or any other non-linear semiconductor array. The EMI filter may be located within the header assembly, the feedthrough assembly, or located proximate to a pulse generator along the energy delivery path.

24 Claims, 4 Drawing Sheets

IMPLANTABLE MEDICAL DEVICE WITH IMPROVED EMI FILTER

FIELD OF THE INVENTION

Embodiments of the present invention pertain generally to implantable medical devices, and more particularly pertain to implantable medical devices that utilize an electromagnetic interference filter to remove unwanted electrical noise.

BACKGROUND OF THE INVENTION

An implantable medical device is implanted in a patient to, among other things, monitor electrical activity of a heart and to deliver appropriate electrical and/or drug therapy, as required. Implantable medical devices ("IMDs") include for example, pacemakers, cardioverters, defibrillators, implantable cardioverter defibrillators ("ICD"), and the like. The electrical therapy produced by an IMD may include, for example, pacing pulses, cardioverting pulses, and/or defibrillator pulses to reverse arrhythmias (e.g. tachycardias and bradycardias) or to stimulate the contraction of cardiac tissue (e.g. cardiac pacing) to return the heart to its normal sinus rhythm.

In general, the IMD includes a battery and electronic circuitry, such as a pulse generator and/or a processor module, that are hermetically sealed within a housing (generally referred to as the "can"). The housing typically is formed of titanium or other suitable corrosion-resistant, biocompatible, electrically conductive material. The housing includes opposed concave half shells that are welded together to form an interior cavity, in which the battery, pulse generator and/or processor module reside. The half shells have an oval contour with a header receptacle area configured to receive a header assembly that is joined to the device housing. A feedthrough assembly is located at the header receptacle area and forms an interface for conductive paths to enter/exit the interior cavity, while maintaining the hermetic seal. Conductor pins are inserted through the feedthrough to provide the conductive paths to and from electronic circuitry.

The header assembly holds a connector block that is configured to be joined to one or more leads that pass into the heart. One end of each lead is inserted into the connector block, while the other end of each lead includes an electrode that is to be positioned in an interior chamber of the heart. The electrode may deliver an electrical shock to defibrillate the heart, or the electrode may provide low energy signals to pace the heart. The electrode may be also used to sense cardiac electrical signals from the heart.

The leads transmit electrical signals between the heart and the pulse generator. In certain environments, a lead may effectively function as an antenna that is susceptible to external electromagnetic (EM) fields. When external electromagnetic fields become coupled to the lead or the connector block, electromagnetic interference ("EMI") signals are generated and injected into the IMD. Patients are exposed to external electromagnetic interference sources in a variety of ways, such as in the home, workplace, public places, and medical facilities. Sources of EMI include cellular telephones (including communication bands for Bluetooth, HomeRF, and wireless LAN), anti-theft devices, keyless entry systems, medical equipment, microwave devices, welding equipment, sources of radio frequency interference (RFI), radio-controlled toys, television broadcast antenna, radio transmitters (e.g. broadcast and two-way), electronic article surveillance systems, and the like.

At specific frequencies, an electromagnetic field may electrically couple with the conductors within the leads, thereby producing an EMI signal that is conveyed along the conductors, through the connector block and feedthrough assembly to the electronic circuitry. The EMI signal may then interfere with the operation of the implanted medical device. For instance, the EMI signal may inhibit pacing or may cause fast, erratic pacing. Further, an EMI signal may resemble a cardiac signal from the heart, which could be misinterpreted by the pulse generator/processor as an event that requires therapy. In turn, the pulse generator may send a pacing or shocking pulse to the heart when not required. In addition, strong EMI signals may cause other problems with the internal electrical circuitry, such as to mistakenly indicate an end-of-battery life, inadvertently reset power-up conditions, cause over-sensing/under-sensing, or cause permanent damage to the circuitry.

To address the above concerns, EMI filter circuits have been designed that attenuate potential EMI signals before reaching the electrical circuitry within the implantable medical device. Conventional EMI filter circuits use "decoupling" capacitors along with surge protection blocks to prevent EMI from damaging the device. One conventional approach prevents EMI from entering the housing of the pulse generator by connecting a capacitor between each conductor pin connected to the sensing circuit or pulse generator and the device's case. Another existing EMI filter removes unwanted noise by shorting the high frequency signal path to the housing through a plurality of capacitors. Other EMI filters add a resistor or a lossy inductor along an energy delivery path, in series with a shunting capacitor.

However, EMI filters that include a series element are generally useful only within dedicated sensing paths or low voltage delivery paths, such as in pacemakers. Such EMI filters are not practical for use in high energy delivery paths, for example, as in defibrillators. Further, EMI filters that include a resistor or lossy inductor may be unable to withstand the high current and or high voltage present in a high-energy delivery path. Hence, a need exists for an EMI filter that is configured to operate in the high energy delivery path of an implantable medical device.

SUMMARY

In accordance with one embodiment, an implantable medical device is provided having a housing with an interior cavity. A feedthrough assembly having a conductor which provides an energy delivery path is joined to the device housing. A control module resides within the interior cavity to regulate the delivery of the energy pulses along the energy delivery path. An electromagnetic interference ("EMI") filter is located along the energy delivery path to attenuate electromagnetic interference. A bypass unit is joined to the EMI filter and configured to at least partially bypass the EMI filter during delivery of the energy pulse.

Optionally, the bypass unit may include a non-linear device joined in parallel with an impedance component. In one embodiment, the non-linear device is a self-triggered device such as a DIAC, or the non-linear device may be a MOSFET, a FET, a bipolar semiconductor transistor, or any other non-linear semiconductor array that can operate as a controlled switch. The EMI filter may be located within the header assembly, or located within the feedthrough assembly, or located proximate to the pulse generator along the energy delivery path.

In accordance with another embodiment, an EMI filtering method is provided for an implantable medical device. The method comprises providing an energy delivery path with a filtering stage and attenuating incoming EMI signals at the filtering stage along the energy delivery path. The method further comprises bypassing at least a portion of the filtering stage during delivery of the energy pulse.

Optionally, the method may include providing, at the filtering stage, an impedance component to attenuate an amplitude characteristic of the EMI signal with respect to frequency. Optionally, the bypassing operation may further include creating a low resistance path for an energy pulse to follow in order to protect a portion of the filtering stage. The bypassing may further include protecting a portion of the filtering stage utilizing a non-linear device that allows passage of the energy pulse. Optionally, the non-linear device may be selected from a group comprising a diode for alternating current (DIAC), a metal oxide semiconductor transistor (MOSFET), an insulated gate field effect transistor (IG-FET), a field effect transistor (FET), an insulated gate bipolar transistor (IGBT), and a bipolar transistor.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

In the following detailed description, reference is made to the accompanying drawings which form a part hereof, and in which is shown by way of illustration specific embodiments in which the present invention may be practiced. These embodiments, which are also referred to herein as "examples," are described in sufficient detail to enable those skilled in the art to practice the invention, and it is to be understood that the embodiments may be combined, or that other embodiments may be utilized and that structural, logical and electrical changes may be made without departing from the scope of the present invention. For example, embodiments may be used with a pacemaker, a cardioverter, a defibrillator, an appetite suppression device, a pain relief device, a muscle stimulation device, a nerve stimulation device and the like. The following detailed description is, therefore, not to be taken in a limiting sense, and the scope of the present invention is defined by the appended claims and their equivalents. In this document, the terms "a" or "an" are used, as is common in patent documents, to include one or more than one. In this document, the term "or" is used to refer to a nonexclusive or, unless otherwise indicated.

Figure 1:
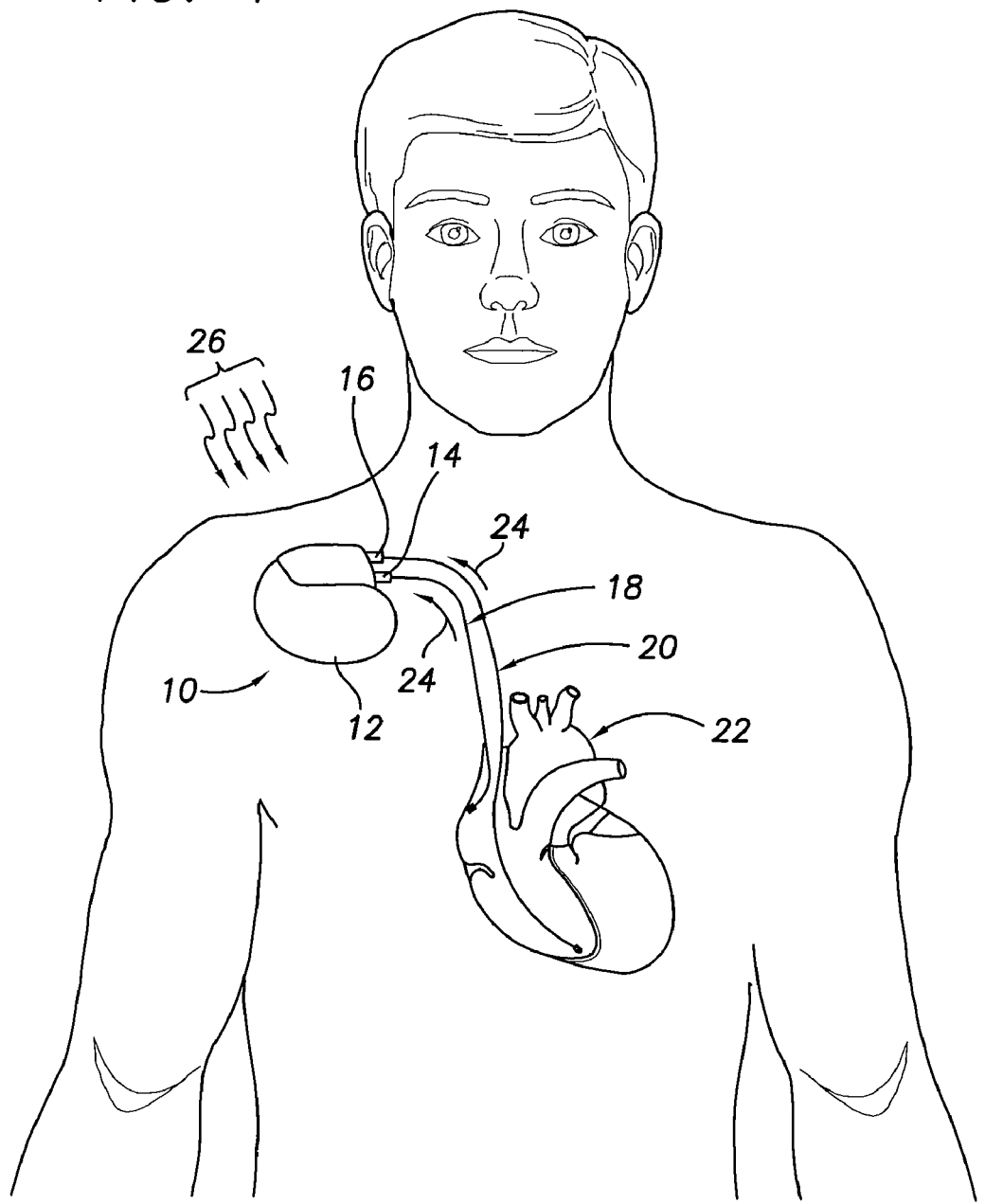
FIG. 1 illustrates an implantable medical device having a set of leads that are configured to be attached to a heart.

FIG. 1 illustrates an implantable medical device 10 that includes a housing 12 that is joined to a header assembly that holds receptacle connectors 14 and 16. The implantable medical device 10 may be a cardiac pacemaker, an implantable cardioverter defibrillator ("ICD"), a defibrillator, an ICD coupled with a pacemaker, an appetite suppression device, a pain relief device, a muscle stimulation device, a nerve stimulation device and the like, implemented in accordance with an embodiment of the present invention. Leads 18 and 20 include proximal ends that are inserted into the receptacle connectors 14 and 16, while distal ends of leads 18 and 20 are implanted within the heart 22. The leads 18 and 20 may be located at various locations, such as an atrium, a ventricle, or both to measure the physiological condition of the heart 22. Based on physiological information detected, the leads 18 and 20 may provide an electric shock to the heart 22. For example, the leads 18 and 20 may function to pace the heart 22, or the leads 18 and 20 may function to provide a high energy electric shock, such as to defibrillate the heart 22. The leads 18 and 20 may provide, a high energy pulse, of 1 to 40 joules of energy as a defibrillation shock to a patient's heart 22. The leads 18 and 20 experience electromagnetic signal 24 from the electromagnetic interference ("EMI") 26 and in certain instances, the EMI 26 may cause electromagnetic signal 24 to flow along the leads 18 and 20. The electromagnetic signals 24 may be transmitted to the housing 12 as in-coming EMI signals and may interfere with the proper functioning of the implantable medical device 10. Similarly, EMI 26 may also induce noise signals at the connector block 34.

Figure 2:
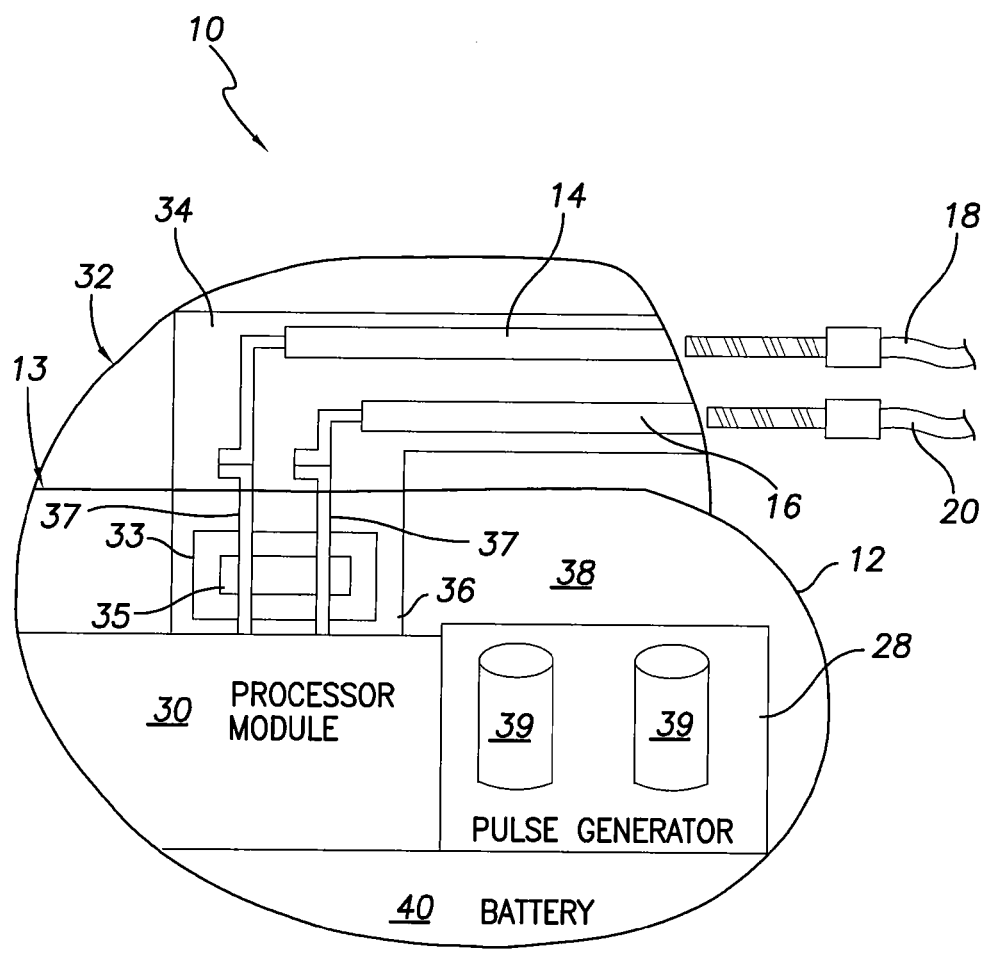
FIG. 2 illustrates a block diagram of certain components of an implantable medical device formed in accordance with an embodiment of the present invention.

FIG. 2 illustrates a block diagram of certain components of the implantable medical device 10. The implantable medical device 10 includes a housing 12, a header assembly 32, a connection block 34, and a feedthrough assembly 36. The housing 12 is typically formed of titanium and includes opposing concave half shells (not shown) that are welded together to form an interior cavity 38. The cavity 38 holds a processor module 30, a pulse generator 28, and a battery 40. The housing 12 may be formed as a closed metal surface that serves as a Faraday cage to screen out sources of EMI 26 (shown in FIG. 1).

The housing 12 includes an oval contour with a header receptacle area 13 configured to receive the header assembly 32 that is mounted securely to the housing 12. The header assembly 32 includes the connection block 34 that holds receptacle connectors 14 and 16, which accept terminal pins 37 on the proximal ends of corresponding leads 18 and 20. The feedthrough assembly 36 is located at the header receptacle area 13 and is hermetically sealed between the half shells of the housing 12 to form an interface into and out of the interior cavity 38. Terminal pins 37 are held within the feedthrough assembly 36 which insulates the terminal pins 37 from the housing 12. Thus, the feedthrough assembly 36 provides an electrical path via conductive terminal pins 37 between the interior cavity 38 of the housing 12 and the exterior of the housing 12. The electrical path may serve to conduct high or low energy pulses to the heart 22 or to convey sense signals from the heart 22. The terminal pins 37 represent conductors that define an energy delivery path from the pulse generator 28 to the connector block 34. In one embodiment, the energy delivery path may be a high energy delivery path that is utilized, for example, by a defibrillator. In an alternative embodiment, the energy delivery path may be a low energy delivery path that is utilized, for example, by a pacemaker.

During manufacturing, the header assembly 32 is attached to the feedthrough assembly 36 after the housing 12 is hermetically sealed. The header assembly 32 is susceptible to the passage of electromagnetic signals 24 and may allow high frequency electromagnetic waves to couple with the energy delivery path leading into the interior cavity 38.

The housing 12 includes a processor module 30 which may typically be a microprocessor, or equivalent control circuitry for processing physiological characteristics of the heart 22. The processor module 30 may further include RAM or ROM memory, logic and timing circuitry, state machine circuitry, and I/O circuitry. Typically, the processor module 30 includes the ability to process or monitor data as controlled by a program code stored in a designated block of memory. The processor module 30 detects a depolarization wave as it spreads through the cardiac tissue and measures the timing, direction of propagation, and point of initiation of successive depolarization waves. The depolarization may be a result of an inherent cardiac cycle or in response to a cardiac pacing event, such as pacing the heart utilizing bi-ventricular pacing, right ventricular pacing, left ventricular pacing, left atrial pacing, right atrial pacing or bi-atrial pacing. The processor module 30 implements an analog-to-digital ("A/D") converter (not shown) and receives raw analog signals that occur during depolarization. The A/D converter converts the raw analog signals to a plurality of digital signals. The digital signals are stored in memory (not shown).

The battery 40 provides the operating power to the electronic components within the housing 12, including the processor module 30. The processor module 30 monitors the heart 22 of a patient based on sense signals received from leads 18 and 20 and detects when the patient is having a post-myocardial infarct, a "silent" myocardial infarct, a myocardial infarct, an ischemia, a heart block, an arrhythmia, fibrillation, congestive heart failure, and the like. Under control of the processor module 30, the processor module 30 provides an electrical stimulation through leads 18 and 20 based on physiological information detected from the sensed signals. For example, the electrical stimulation may be provided to the heart 22 when the intrinsic heartbeat is insufficient, when depolarization is not properly conducted through the heart 22, or when a heart rate is too slow to maintain adequate blood from the heart 22 to the remainder of the body, and the like.

In addition, the processor module 30 detects electrical characteristics of heart 22 and controls preventative pacing schemes such as bi-ventricular, right ventricular, left ventricular, left atrial, right atrial, and bi-atrial pacing. By monitoring the excitability of cardiac tissue and the response to different pacing schemes, the processor module 30 is able to provide a physician with information as to the patient's physiological condition, e.g., whether it has improved or is progressing towards cardiac failure.

Electromagnetic signals 24 that are introduced into leads 18 and 20 and/or wires (not shown) on connector block 34 are transmitted to the housing 12. Electromagnetic signals 24 can induce high-speed transients in the internal circuitry of IMD 10. The induced electromagnetic signals 24 may cause the electronic components, such as the processor module 30, to malfunction. An EMI filter 35 is located along the energy delivery path, such as along the terminal pins 37. The EMI filter 35 forms a filtering stage and attenuates electromagnetic interference signals that travel through the connector block 34 and attempt to enter the interior cavity 38 through the feedthrough assembly 36. A bypass unit 33 is joined to the EMI filter 35 and switches between a closed-circuit state and an open circuit state. The change in the state of the bypass unit 33 can be achieved by using, in one embodiment a self-triggered device; or in an alternative embodiment a controlled device, the later requiring a control signal supplied by the pulse generator 28 or the processor module 30. The bypass unit 33 forms a low resistance path, when in a closed circuit state, that at least partially bypasses the EMI filter 35, at the filtering stage, when an energy pulse is delivered from the pulse generator 28, through the feedthrough assembly 36 and connector block 34 to the leads 18 and 20. A remainder of the time, the bypass unit 33 maintains an open circuit state. When the bypass unit 33 is in the open circuit state, the signals carried by the terminal pins 37 do not bypass the passive elements located in EMI filter 35.

The electronic EMI filter 35 is utilized to attenuate the electromagnetic signals 24, thereby protecting the electronic components within the housing 12. The EMI filter 35 blocks electromagnetic signals 24 from EMI sources 26 from entering the housing 12 of the implantable medical device 10. The EMI filter 35 may be composed of passive electronic components such as resistors, capacitors and inductors. The passive components contain a resistive component. The inductor and the capacitor also have a component termed reactance. The reactance's magnitude of a capacitor, XC, is defined as $XC=1/(2\pi f*C)$, and the reactance's magnitude of an inductor, XL, is defined as $XL=2\pi f*L$. When a direct current is applied to a capacitor, the capacitor behaves as an open circuit. As the frequency of the applied signal increases, a capacitor tends to behave as a short circuit. A capacitor can be used to short circuit or to bypass undesirable high frequency signals. Thus, a capacitor may act as a low pass filter that blocks high frequency signals but allows low frequency signals to pass. An inductor behaves opposite compared to a capacitor. For example, inductive reactance, XL, increases in value with increasing frequency compared to capacitive reactance, XC. When direct current is passed through an inductor, inductive reactance is zero and linearly grows as the frequency increases.

Table 1 shows how the impedance value of a capacitor and inductor change with frequency. Impedance is the total "resistance" of a capacitor or inductor combined with a resistive component of the electrical circuit. An impedance of a circuit containing a resistor and a capacitor is calculated as ZC=Square Root ($|R|2+|XC|2$), and a circuit containing a resistor and an inductor is calculated as ZL=Square Root ($|R|2+|XL|2$); where R is the value of a resistor in the circuit. If no resistor is present, the value of R equals zero. The impedance value indicates whether the component is behaving as an open circuit (e.g. large Ohm value) or a short circuit (e.g. almost zero Ohm value). A capacitor behaves as an open circuit at low frequencies and a short circuit at higher frequencies. An inductor behaves just the opposite, for example, it behaves as a short circuit at low frequencies and as an open circuit at high frequencies.

TABLE 1

| Reactance | For example, for: | $|X|(f)$ is: |
|---|---|---|
| $|X_C| = 1/(2 * \pi * f * C)$ | C = 1 microfarad<br>f = frequency in MHz; | $|X_C|$ = infinite Ω @ DC (an open circuit)<br>$|X_C|$ = 159.2Ω @ 1 KHz<br>$|X_C|$ = 0.159Ω @ 1 MHZ<br>$|X_C|$ = 0.00159Ω @ 100 MHz (a short circuit) |
| $|X_L| = 2 * \pi * f * L$ | L = 100 microHenries<br>f = frequency in MHz | $|X_L|$ = 0Ω (short circuit) @ DC<br>$|X_L|$ = 0.628Ω @ 1 KHz |

TABLE 1-continued

| Reactance | For example, for: | \|X\|(f) is: |
|---|---|---|
| | | $\|X_L\| = 628.3\Omega$ @ 1 MHz |
| | | $\|X_L\| = 62.83K\Omega$ @ 100 MHz |

The EMI filter 35 may be passive, consume low power, and small in size. For example, the EMI filter 35 may utilize chip capacitors incorporated in the feedthrough 36 to protect the electronic components in the housing 12 from electromagnetic signals 24. Chip capacitors are capacitors without leads and are also known as surface mount capacitors. A disadvantage of chip capacitors is that they occupy needed space. Further, the signal traces required to connect the chip capacitors to the electronics within implantable medical device 10 are subject to stray inductances that diminish the high frequency performance of the chip capacitor. Typically, a chip capacitor is positioned between the connector terminal of the feedthrough assembly 36 and the housing 12, or the chip capacitor may be positioned outside the housing 12. When the chip capacitor is located near the housing 12, a portion of the capacitor is covered with a biocompatible material to prevent bodily fluids from entering the housing 12. Further, as a passive element, a number of chip capacitors may be used to adequately attenuate the electromagnetic signal 24.

Passive components connected to an energy delivery path must be able to sustain the corresponding power dissipated through the component. For instance, an electronic component connected in series with a high energy delivery path may be suitable only for a low voltage-low amperage signal. An electronic component such as a passive resistor may not be suitable to accommodate a high-energy pulse of several hundred volts transmitted as a shocking pulse to the heart 22. The instantaneous power dissipated across such a passive resistor is defined as $p=i^2R$ or $p=v^2/R$. So, the power across the component is equivalent to the square of the current or voltage through/across the component. Such a large current pulse could destroy a component. Thus, a resistor can be damaged if exposed to high energy pulses of short duration because the maximum allowable temperature of the resistor is surpassed. In the following diagrams, the arrows indicating direction show generator-load relationships, not electronic current direction.

Figure 3:
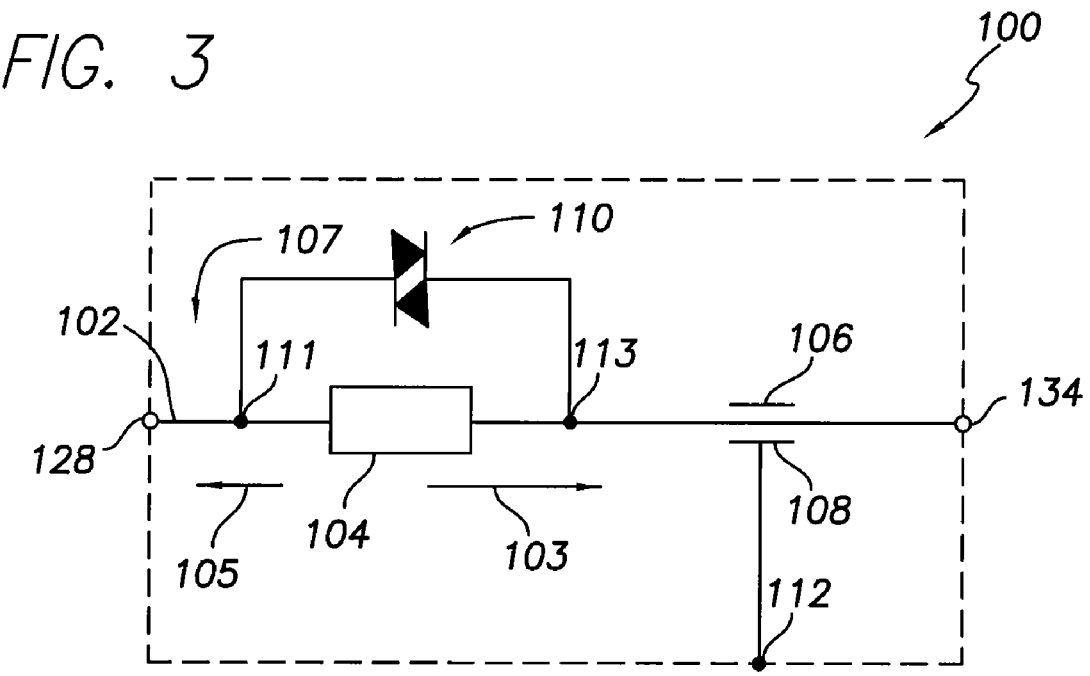
FIG. 3 illustrates a schematic diagram of an electromagnetic interference filter formed in accordance with an embodiment of the present invention.

FIG. 3 illustrates a schematic diagram of an EMI filter 100 in accordance with one embodiment of this invention. In one embodiment, the EMI filter 100 is positioned along a high energy delivery path 102 between a lead connector block 34 (shown in FIG. 2) at node 128 and a pulse generator 28 (shown in FIG. 2) at node 134. EMI filter 100 includes an impedance element 104 joined in series with a capacitor 106 that has one plate 108 connected to a housing 112 of implantable medical device 10 (shown in FIG. 1). In one embodiment, the impedance element 104 is a resistor. In another embodiment, the impedance element 104 is an inductor. Alternatively, in another embodiment, the impedance element 104 is an inductor joined in series with a resistor. Further, depending up method of manufacturing and construction, capacitor 106 may have many plates. In one embodiment, capacitor 106 can be a surface mount capacitor. In another embodiment, capacitor 106 may be monolithically integrated into the feedthrough 36 (shown in FIG. 2). In one embodiment, a DIAC 110 is connected at node 111 and node 113 such that DIAC 110 is connected in parallel across the impedance element 104. The DIAC 110 is bidirectional trigger diode that exhibits a high resistance to signals whose amplitudes are below the device's threshold level. When the threshold voltage has been exceeded, the DIAC becomes a closed circuit. Until the threshold voltage is exceeded, the DIAC 110 remains in a high-resistance, non-conducting state.

Figure 4:
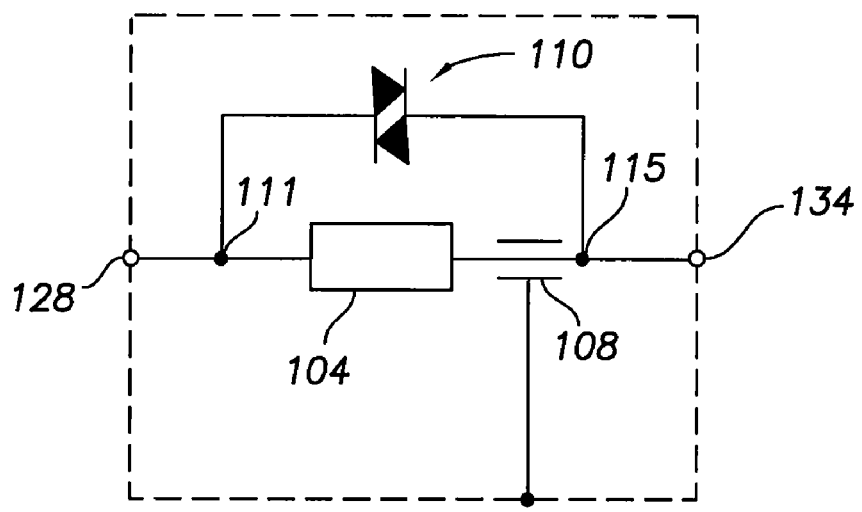
FIG. 4 illustrates a schematic diagram depicting an alternative connection for the EMI filter of FIG. 3 in accordance with an embodiment of the present invention.

FIG. 4 illustrates another embodiment of EMI filter 100 (shown in FIG. 3), where DIAC 110 is connected at node 111 and node 115 such that DIAC 110 is connected in parallel across both impedance element 104 and capacitor 108.

Referring back to FIG. 3, sensed signals and EMI signals 24 enter the lead connection block 34 (shown in FIG. 2) at node 128 in the direction of arrow 103. The capacitance value of the capacitor 106 is chosen to short the high frequency spectrum of the EMI signals 24 to the housing 112. The capacitor 106 remains an open circuit for low frequency sensed signals, thereby allowing the low frequency sensed signals through the impedance element 104. In one embodiment, impedance element 104 is a resistor. When the resistor is joined with capacitor 106, the value of the resistor determines the "corner frequency" of the resistor-capacitor (RC) filter. The value of the resistor is chosen such that most of the EMI signal 24 spectrum is substantially attenuated, while the low frequency sensed signals are only slightly attenuated.

Arrow 105 shows the direction of an energy pulse when a plurality of shocking capacitors 39 (shown in FIG. 2), controlled by the processor module 30 discharge the pulse along the high energy delivery path 102. In one embodiment, the pulse is a high energy pulse that originates from a defibrillator. In an alternative embodiment, the pulse is a low energy pulse that originates from a pacemaker. When the magnitude of the voltage across the DIAC 110 exceeds a breakdown voltage, the DIAC 110 changes from a non-conducting state to a conducting state. In the conductive state, the DIAC 110 allows the energy pulse to bypass the impedance element 104 along path 107 and be transmitted along the energy delivery path 102 to node 128 that is joined to connector block 34 (shown in FIG. 2). Path 107 represents a low resistance path. In an alternative embodiment, EMI filter 100 may be positioned within the header assembly 32 (shown in FIG. 2). In a further alternative embodiment, EMI filter 100 may be positioned within the interior cavity 38 (shown in FIG. 2) of the housing 12 (shown in FIG. 2). In yet another alternative embodiment, the DIAC 110 can be replaced by any non-linear controlled device such as a metal-oxide-semiconductor field-effect transistor (MOSFET), an insulated-gate field effect transistor (IGFET), a field effect transistor (FET), an insulated gate bipolar transistor (IGBT), a bipolar transistor, and the like.

Figure 5:
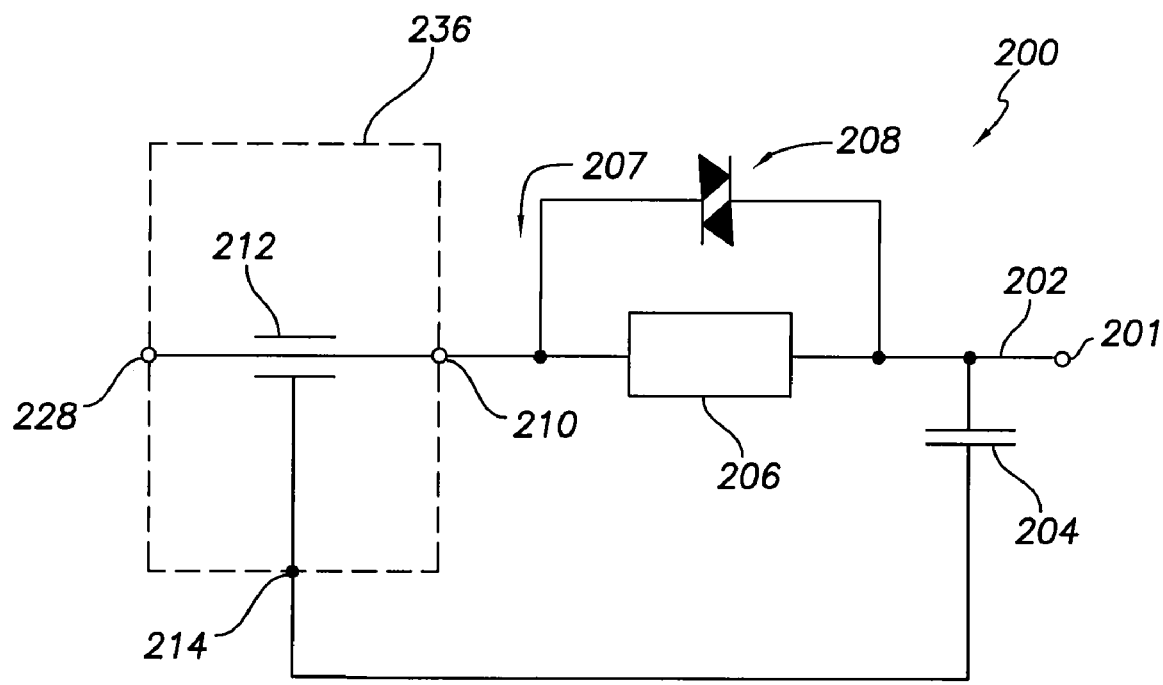
FIG. 5 illustrates a schematic diagram of another electromagnetic interference filter including a non-linear device formed in accordance with an embodiment of the present invention.

FIG. 5 illustrates a schematic diagram of an EMI filter 200 that is formed in accordance with an alternative embodiment. The EMI filter 200 is positioned adjacent to a feedthrough assembly 236 which is coupled to a lead connector block 34 (shown in FIG. 2) at node 228. The EMI filter 200 includes a capacitor 204, an impedance element 206 and a DIAC 208 located along an energy delivery path 202. The EMI filter 200 is joined to the feedthrough assembly 236 at node 210 and to a pulse generator 28 (shown in FIG. 2) and/or sensing circuitry (not shown) at node 201. The feedthrough assembly 236 includes a capacitor 212 that is connected to the housing 214 of the implantable medical device 10 (shown in FIG. 1). In another embodiment, the feedthrough assembly 236 does not include a filter. In still another embodiment, the feedthrough assembly may include a filter, such as a single-capacitor. The impedance element 206 is connected in series between the feedthrough assembly 236 and the capacitor 204. The impedance element 206 combined with capacitor 204 forms a low pass filter that attenuates most of the EMI signals 24. The DIAC 208 is connected across the impedance element 206. In yet another alternative embodiment, the DIAC 208 can be replaced by any non-linear controlled device such as a metal-oxide-semiconductor field-effect transistor (MOSFET), an insulated-gate field effect transistor (IGFET), a field effect transistor (FET), an insulated gate bipolar transistor (IGBT), a bipolar transistor, and the like.

When the pulse generator 28 delivers a high-energy pulse, the DIAC 208 acts as a bypass to allow the passage of an energy pulse from the pulse generator 28 (shown in FIG. 2) along the energy delivery path 202 to node 228. In one embodiment, a defibrillator delivers a high energy pulse along path 202 to node 228. In an alternative embodiment, a pacemaker delivers a low energy pulse along path 202 to node 228. DIAC 208 switches states to control the passage of the energy pulse along the energy delivery path 202. When the voltage across DIAC 208 is less than a threshold voltage, DIAC 208 is in a non-conductive state (e.g. switch is open). In the non-conductive state, DIAC 208 has a very large input impedance that prevents signals from flowing through the device. When the voltage across DIAC 208 is greater than the required threshold voltage, DIAC 208 changes from a non-conductive state to a conductive state (e.g. switch is closed). In the conductive state, the DIAC 208 allows the energy pulse to bypass impedance element 206 along path 207 and be transmitted to node 228.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects.

What is claimed is:

1. An implantable medical device, comprising:
   a housing defining an interior cavity;
   a feedthrough assembly joined to the housing, the feedthrough assembly including at least one conductor to define an energy delivery path;
   a pulse generator adapted to generate an energy pulse;
   a control module, within the interior cavity, to regulate the delivery of the energy pulse along the energy delivery path;
   an EMI filter, located along the energy delivery path, to attenuate electromagnetic interference; and
   a bypass unit joined to the EMI filter, the bypass unit switching to a closed circuit state, during delivery of the energy pulse, to direct the energy pulse to at least partially bypass the EMI filter, the bypass unit switching to an open circuit state, when the energy pulse is not delivered, to direct EMI signals received at the feedthrough assembly from the at least one conductor through the EMI filter.

2. The device of claim 1, wherein the EMI filter includes an impedance component and the bypass unit includes a non-linear component joined in parallel with the impedance component.

3. The device of claim 1, wherein the bypass unit includes a non-linear component that is selected from a group comprising a diode for alternating current (DIAC), a metal oxide semiconductor (MOSFET) transistor, an insulated gate field effect transistor (IGFET), a field effect transistor (FET), an insulated gate bipolar transistor (IGBT), and a bipolar transistor.

4. The device of claim 1, wherein the bypass unit includes a non-linear component that provides a low resistance path along the energy delivery path during delivery of the energy pulse.

5. The device of claim 1, wherein the EMI filter includes an impedance component that includes at least one of a resistor, a capacitor, an inductor, and a combination thereof.

6. The device of claim 5, wherein the energy pulse has a current capable of exceeding a power dissipation capacity of the impedance component when said impedance component is connected in series to the energy delivery path.

7. The device of claim 1, wherein the EMI filter includes an impedance component that includes a resistor and a capacitor joined in series, the resistor connected to a connector block joined to the housing and the capacitor internally grounded.

8. The device of claim 1, wherein the EMI filter includes a first capacitor, a second capacitor, and a resistor, the first capacitor joined to the second capacitor at a node, the node internally grounded to the housing, the resistor connected in series between the first capacitor and the second capacitor.

9. The device of claim 1, further comprising a header provided on the housing, the EMI filter positioned within the header and proximate to the feedthrough assembly.

10. The device of claim 1, wherein the EMI filter is positioned within the feedthrough assembly.

11. The device of claim 1, further comprising a pulse generator in the interior cavity, wherein the EMI filter is positioned in the interior cavity between the feedthrough assembly and the pulse generator.

12. The device of claim 1, wherein the control module further includes electronic components and a pulse generator located within the interior cavity, the electronic components detect a physiological condition of a body, the pulse generator delivering therapy to the body.

13. The device of claim 1, wherein the implantable medical device comprises a cardiac pacemaker, an implantable defibrillator, a ventricular assist device, an implantable cardioverter defibrillator, an appetite suppression device, a pain relief device, a muscle stimulation device, or a nerve stimulation device.

14. A method of providing EMI filtering for an implantable medical device, the method comprising:
   providing an energy delivery path with a filtering stage and a bypass path, the bypass path located in parallel with and bypassing the filtering stage;
   attenuating EMI signals at the filtering stage along the energy delivery path when the bypass path is in an open circuit state; and
   bypassing at least a portion of the filtering stage along the conductive path during delivery of an energy pulse when the bypass path is in a closed circuit state.

15. The method of claim 14, wherein the attenuating includes decreasing an amplitude of the EMI signal to limit interference with operation of the implantable medical device.

16. The method of claim 14, wherein the attenuating includes decreasing the speed of change of the EMI signal to limit interference with operation of the implantable medical device.

17. The method of claim 14, wherein the bypassing further includes creating a low resistance path for the energy pulse to protect the filtering stage.

18. The method of claim 14, wherein the bypassing further includes protecting a portion of the filtering stage utilizing a non-linear device that passes the energy pulse.

19. The method of claim 14, wherein the providing includes providing a non-linear device along the conductive path that allows passage of the energy pulse.

20. An implantable medical device comprising:
   a housing;
   a lead extending from the housing and positioned proximate to a heart;
   a pulse generator electrically coupled with the lead by an energy delivery path, the pulse generator configured to supply an energy pulse along the lead to the heart;
   an EMI filter located along the energy delivery path and adapted to attenuate electromagnetic interference; and
   a bypass unit located along a conductive path that is coupled with the energy delivery path, wherein the bypass unit is adapted to open and close a circuit comprising the conductive path and the pulse generator, the bypass unit closing the circuit to direct the energy pulse around the EMI filter and to the heart.

21. The device of claim 20, wherein the bypass unit opens the circuit comprising the conductive path and the pulse generator to direct electromagnetic interference to the EMI filter.

22. The device of claim 20, wherein the bypass unit is a self-triggered device that alternates between open and closed states to open and close the circuit, respectively.

23. The device of claim 20, wherein the bypass unit is adapted to open and close the circuit based on an amplitude of the energy pulse.

24. The device of claim 20, wherein the EMI filter and the bypass unit are disposed within the housing.

* * * * *

UNITED STATES PATENT AND TRADEMARK OFFICE
CERTIFICATE OF CORRECTION

PATENT NO. : 7,620,453 B1
APPLICATION NO. : 11/551664
DATED : November 17, 2009
INVENTOR(S) : Propato et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 428 days.

Signed and Sealed this

Twenty-sixth Day of October, 2010

David J. Kappos
*Director of the United States Patent and Trademark Office*